US010501432B2

(12) United States Patent
Runco et al.

(10) Patent No.: US 10,501,432 B2
(45) Date of Patent: Dec. 10, 2019

(54) CHIRAL SEPARATION OF $\Delta^8$-THC, $\Delta^9$-THC, AND RELATED ENANTIOMERS USING $CO_2$-BASED CHROMATOGRAPHY

(71) Applicant: Waters Technologies Corporation, Milford, MA (US)

(72) Inventors: Jacquelyn Runco, Delmont, PA (US); Andrew Aubin, Taunton, MA (US); John A. Mackay, Whitinsville, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/473,868

(22) Filed: Mar. 30, 2017

(65) Prior Publication Data

US 2017/0283391 A1  Oct. 5, 2017

Related U.S. Application Data

(60) Provisional application No. 62/316,754, filed on Apr. 1, 2016.

(51) Int. Cl.
| | |
|---|---|
| *C07D 311/80* | (2006.01) |
| *B01D 15/42* | (2006.01) |
| *B01D 15/40* | (2006.01) |
| *B01D 15/16* | (2006.01) |
| *B01J 20/32* | (2006.01) |
| *B01J 20/29* | (2006.01) |
| *B01J 20/28* | (2006.01) |
| *B01J 20/10* | (2006.01) |
| *B01J 20/24* | (2006.01) |

(52) U.S. Cl.
CPC .......... *C07D 311/80* (2013.01); *B01D 15/166* (2013.01); *B01D 15/40* (2013.01); *B01D 15/426* (2013.01); *B01J 20/103* (2013.01); *B01J 20/24* (2013.01); *B01J 20/28004* (2013.01); *B01J 20/29* (2013.01); *B01J 20/3204* (2013.01); *B01J 20/3231* (2013.01); *B01J 20/3293* (2013.01); *B01J 2220/46* (2013.01); *B01J 2220/54* (2013.01); *C07B 2200/07* (2013.01); *C07B 2200/09* (2013.01)

(58) Field of Classification Search
CPC . C07D 311/80; B01J 20/3293; B01J 20/3231; B01J 20/3204; B01J 20/29; B01J 20/28004; B01J 20/103; B01J 20/24; B01J 2220/46; B01J 2220/54; B01J 2200/09; B01D 15/40; B01D 15/166; B01D 15/426; C07B 2200/09; C07B 2200/07
See application file for complete search history.

(56) References Cited

U.S. PATENT DOCUMENTS

| | | | |
|---|---|---|---|
| 4,017,528 | A | 4/1977 | Unger et al. |
| 5,374,755 | A | 12/1994 | Neue et al. |
| 6,686,035 | B2 | 2/2004 | Jiang et al. |
| 7,223,473 | B2 | 5/2007 | Jiang et al. |
| 7,919,177 | B2 | 4/2011 | Jiang et al. |
| 2014/0157871 | A1 | 6/2014 | Dubant et al. |
| 2015/0331001 | A1 | 11/2015 | Jones et al. |

FOREIGN PATENT DOCUMENTS

| | | |
|---|---|---|
| WO | 2010/141426 A1 | 12/2010 |
| WO | 2013/134468 A1 | 9/2013 |
| WO | 2013/134471 A1 | 9/2013 |
| WO | 2013/134473 A1 | 9/2013 |
| WO | 2013/134475 A1 | 9/2013 |
| WO | 2013/134476 A1 | 9/2013 |
| WO | 2013/134478 A1 | 9/2013 |
| WO | 2013/134483 A1 | 9/2013 |
| WO | 2013/134485 A1 | 9/2013 |
| WO | 2013/134496 A2 | 9/2013 |

OTHER PUBLICATIONS

Engda, A., "Supercritical Fluid Chromatography and Enhanced Fluidity Liquid Chromatography: Green Alternatives to Conventional Liquid Chromatography". 2014Ghent, Belgium: Ghent University. Faculty of Sciences:1-163.*
West, C.,"Enantioselective separations with supercritical fluids-review." Current Analytical Chemistry 10.1 (2014): 99-120.*
Diacel Chiral Technologies (Instruction Manual for Chiralpak® AD-H, Supercritical Fluid Chromatography (SFC), 2014 p. 1-4.*
Biba, M., "Effect of particle size on the speed and resolution of chiral separations using supercritical fluid chromatography." Journal of Chromatography A 1363 (2014): 250-256.*
Chester, T. L., "Supercritical fluid chromatography and extraction." Analytical chemistry 70.12 (1998): 301R-320R.*
Berger, T. A. "Supercritical Fluid Chromatography. Primer. Document# 5991e5509EN. Agilent Technologies." Inc., USA (2015).*
World Health Organization "Proposal for Revision of High Performance Liquid Chromatogaphy" Working document QAS/12.476; Jul. 2012 p. 1-16.*
Levin et al. Resolution of chiral cannabinoids on amylose tris(3,5-dimethylphenylcarbamate) chiral stationary phase: effects of structural features and mobile phase additives. J Chromatogr A. 654(1):53-64 (1993).
Perrotin-Brunel et al. Supercritical fluid extraction of cannabis: experiments and modeling of the process design. Retrieved from <isasf.net/fileadmin/files/Docs/Graz/HtmlDir/Papers/CO68.pdf> on Jan. 1, 2016 (6 pages).

(Continued)

*Primary Examiner* — John M Mauro
(74) *Attorney, Agent, or Firm* — Womble Bond Dickinson (US) LLP; Deborah M. Vernon; Rebecca N. Barnes

(57) ABSTRACT

The present disclosure generally relates to methods for separating $\Delta^8$-THC, $\Delta^9$-THC, and related enantiomers using $CO_2$-based chromatography.

13 Claims, 7 Drawing Sheets

(56) References Cited

OTHER PUBLICATIONS

Ruppel et al. Cannabis Analysis: Potency testing identification and quantification of THC and CBD by GC/FID and GC/MS. Gas Chromatography/Mass Spectrometry. Perkin Elmer, Inc.: Shelton, Conneticut (6 pages) 2015.

Tarbox et al. (Nov. 2009) A Validated Chiral HPLC Method for Resolution of delta 8 and delta 9-tetrahydrocannabinol Enantiomers. Poster session presented at the EAS, Round Rock ,TX. Cerilliant Corporation. Retrieved from <cerilliant.com/newsAndEvents/posterArticle.aspx?ID=12> on Mar. 10, 2016 (Abstract Only).

Tarbox et al. (Nov. 2009) A Validated Chiral HPLC Method for Resolution of delta 8 and delta 9-tetrahydrocannabinol Enantiomers. Poster session presented at the EAS, Round Rock ,TX. Cerilliant Corporation (Poster).

De Klerck et al. "Supercritical fluid chromatography for the enantioseparation of pharmaceuticals." J. Pharma. Biomed. Anal. 62(2012):77-92.

"7 Proven Medical Benefits of THC." In Leaf Science, Jul. 22, 2014. Retrieved Mar. 10, 2016. www.leafscience.com/2014/07/227/-proven-medical-benefits-thc/.

"Cesamet™ (nabilone)." Valeant Pharmaceuticals International, Part No. 12-1391. Revised May 2006.

"Marinol (dronabinol)." FDA Listing, Reference ID: 4145204. Revised: Aug. 2017.

"Medical cannabis." In Wikipedia. Retrieved Mar. 10, 2016. en.wikipedia.org/wiki/Medical_cannabis.

Abbott. "The Synthetic Routes of Tetrahydrocannabinaol." Utica College, Dept. Chem. Biochem. Apr. 15, 2014.

Bermudez-Silva et al. "The endocannabinoid system, eating behavior and energy homeostatis: The end or a new beginning?" Pharmacol. Biochem. Behavior. 95(2010): 375-382.

Hanson et al. "Polymer-coated reversed-phase packings in high-performance liquid chromatography." J. Chromatogr. A. 656(1993): 369-380.

Hillig et al. "Genetic evidence for speciation in Cannabis (Cannabaceae)." Gen. Res. Crop Eval. 52(2005):161-180.

* cited by examiner

CHIRAL SEPARATION OF Δ⁸-THC, Δ⁹-THC, AND RELATED ENANTIOMERS USING CO₂-BASED CHROMATOGRAPHY

RELATED APPLICATIONS

This application claims priority to U.S. Provisional Application No. 62/316,754, filed Apr. 1, 2017, the entire contents of which are incorporated herein by reference.

TECHNICAL FIELD

The present disclosure generally relates to methods for separating $\Delta^8$-THC, $\Delta^9$-THC, and related enantiomers using $CO_2$-based chromatography.

BACKGROUND

Cannabinoids, such as tetrahydrocannabinol (THC), have gained considerable attention over the past decade for use in treating various conditions such as chronic pain, muscle spasms, chemotherapy induced nausea and vomiting, anorexia, and post-traumatic stress disorder. See e.g., Pharmacology Biochemistry and Behavior 2010, 95 (4): 573-82, Genetic Resources and Crop Evolution 52: 161-180, 2005, and the United States Food and Drug Administration (FDA) approved listing for synthetic cannabinoids Nabilone and Dronabinol. Evidence also suggests that cannabinoids may increase appetite in HIV/AIDS patients, improve sleep, decrease side effects associated with Tourette syndrome, improve asthma and glaucoma, and treat neurological conditions such as multiple sclerosis and epilepsy. Despite these numerous implications, the full therapeutic potential of cannabinoids, e.g., in medicinal cannabis therapies, has yet to be realized.

THC, or more precisely its major isomer (−)trans-$\Delta^9$-THC, is perhaps the single most therapeutically active cannabinoid present in medical marijuana. THC exists in eight isomeric forms, four of which are predominant and include (+)trans-$\Delta^8$-THC, (−)trans-$\Delta^8$-THC, (+)trans-$\Delta^9$-THC, and (−)trans-$\Delta^9$-THC. The remaining four cis isomers are essentially non-existent in nature and are highly unstable. One of the problems associated with studying THC has been the lack of efficiency in isolating and separating the predominant isomers. For example, conventional normal phase HPLC methods typically do not achieve baseline resolution and have run times typically greater than 20 min.

This challenging problem is important to solve particularly when regulatory bodies such as the FDA require stereoisomeric quantification of drug substances. In addition, chiral separation of THC constituents is also important in legal matters, e.g., to establish the presence or absence of potentially illegal substances, or to create an enanteomeric profile (fingerprint) of the illegal substance, including enanteomeric excess. The need therefore exists to develop a reliable high-throughput method for optimally separating (+)trans-$\Delta^8$-THC, (−)trans-$\Delta^8$-THC, (+)trans-$\Delta^9$-THC, or (−)trans-$\Delta^9$-THC from a sample.

SUMMARY

The present disclosure generally relates to robust, high-throughput, and industrially applicable methods for separating the predominant isomers of THC selected from (+)trans-$\Delta^8$-THC, (−)trans-$\Delta^8$-THC, (+)trans-$\Delta^9$-THC, and (−)trans-$\Delta^9$-THC, using $CO_2$-based chromatography.

The disclosed methods provide more efficient means for separating the predominant isomers of THC, which include e.g., faster run times and better resolution.

The disclosed methods not only solve the problem in separating the predominant isomers of THC (see e.g., FIG. 1), but also eliminate the need for multiple chromatographic runs, minimize the consumption of mobile phase solvent and decrease waste, and reduce the cost of analysis per sample. Thus, the present methods solve both the problem associated with studying THC by providing high-throughput and robust means for separating predominant isomers of THC and, in addition, have beneficial properties over chromatographic methods that employ traditional solvent systems.

DETAILED DESCRIPTION OF CERTAIN EMBODIMENTS

Figure 1:
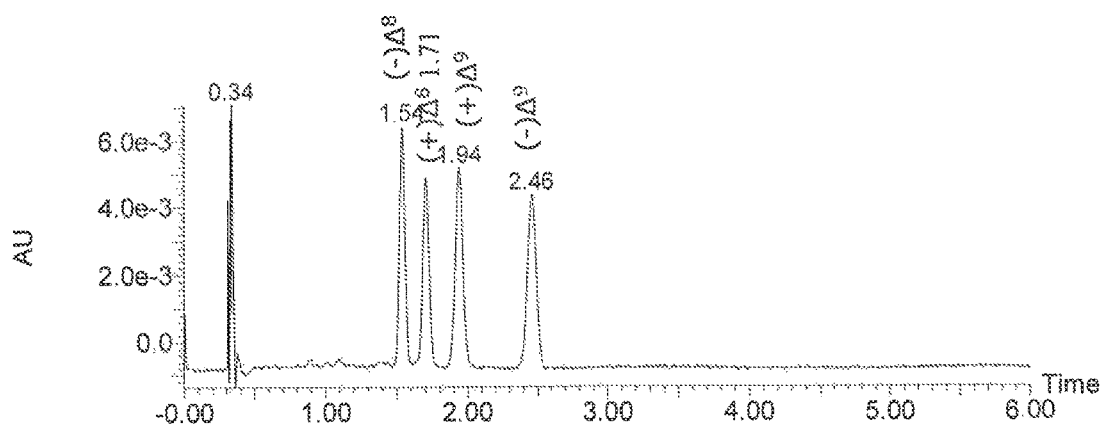
FIG. 1 depicts a chromatogram of the separation of (+)trans-$\Delta^8$-THC, (−)trans-$\Delta^8$-THC, (+)trans-$\Delta^9$-THC, and (−)trans-$\Delta^9$-THC using a Trefoil AMY1 column and 15% ethanol following the $CO_2$-based chromatography methods described herein.

In one embodiment, provided are methods for separating an isomer of THC selected from (+)trans-$\Delta^8$-THC, (−)trans-$\Delta^8$-THC, (+)trans-$\Delta^9$-THC, and (−)trans-$\Delta^9$-THC using $CO_2$-based chromatography, comprising applying a sample comprising the isomer of THC; and eluting the isomer of THC from the chromatography column using a mobile phase comprising $CO_2$.

(+)trans-$\Delta^8$-THC refers to (6aS,10aS)-1,6,6,9-tetramethyl-3-pentyl-6a,7,10,10a-tetrahydro-6H-benzo[c]chromene having the structure:

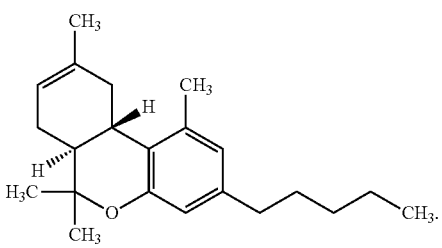

Unless otherwise specified, (+)trans-Δ⁸-THC, (+)Δ⁸, and (+)Δ⁸-THC are used interchangeably and each refer to the trans structure shown above.

(−)trans-Δ⁸-THC refers to (6aR,10aR)-1,6,6,9-tetramethyl-3-pentyl-6a,7,10,10a-tetrahydro-6H-benzo[c]chromene having the structure:

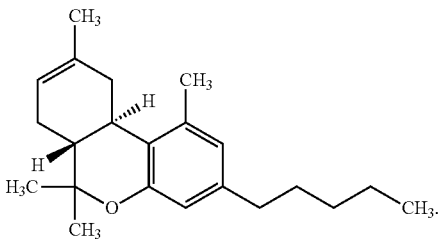

Unless otherwise specified, (−)trans-Δ⁸-THC, (−)Δ⁸, and (−)Δ⁸-THC are used interchangeably and each refer to the trans structure shown above.

(+)trans-Δ⁹-THC refers to (6aS,10aS)-1,6,6,9-tetramethyl-3-pentyl-6a,7,8,10a-tetrahydro-6H-benzo[c]chromene having the structure:

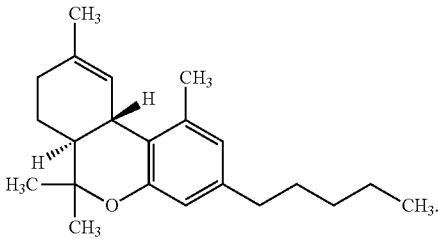 [SMILES: CCCCCc1cc(C)c2c(c1)OC(C)(C)[C@H]1CCC(C)=C[C@H]21]

Unless otherwise specified, (+)trans-Δ⁹-THC, (+)Δ⁹, and (+)Δ⁹-THC are used interchangeably and each refer to the trans structure shown above.

(−)trans-Δ⁹-THC refers to (6aR,10aR)-1,6,6,9-tetramethyl-3-pentyl-6a,7,8,10a-tetrahydro-6H-benzo[c]chromene having the structure:

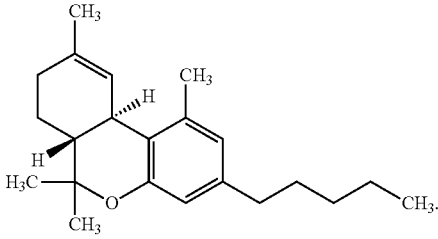

Unless otherwise specified, (−)trans-Δ⁹-THC, (−)Δ⁹, and (−)Δ⁹-THC are used interchangeably and each refer to the trans structure shown above.

The $CO_2$ in the methods described herein (e.g., in the mobile phase) can be in one or more physical states. For example, in one embodiment, the $CO_2$ is in liquid form. In another embodiment, the $CO_2$ is a supercritical liquid or in a subcritical liquid state, or both.

Due to its miscibility, the $CO_2$ mobile phase can be combined with one or more modifiers (co-solvents) to improve desorption or elution of the isomers of THC described herein. Thus, in one embodiment, the mobile phase comprising $CO_2$ in the methods described herein further comprises a modifier. Suitable modifiers include e.g., polar water-miscible organic solvents, such as methanol, ethanol, isopropanol, acetonitrile, acetone, and tetrahydrofuran, or mixtures of water and any of these solvents. In one embodiment, the modifier used in the present methods is methanol or ethanol. In one embodiment, the modifier is ethanol. In a further embodiment, the mobile phase described herein is a mixture of $CO_2$ and ethanol.

Optimal amounts of modifiers, mixtures thereof, as well as the amounts and gradients of $CO_2$ and modifiers used in the separation methods depends upon e.g., the sample and column features, and would be apparent to one of skill in the art. Thus, in one embodiment, for example, the modifier described herein (e.g., methanol or ethanol) is present in an amount ranging from 1% to 30% per total volume of the mobile phase. In another embodiment, the modifier described herein (e.g., methanol or ethanol) is present in an amount ranging from 3% to 25% per total volume of the mobile phase. In another embodiment, the modifier described herein (e.g., methanol or ethanol) is present in an amount ranging from 5% to 20% per total volume of the mobile phase. In another embodiment, the modifier described herein (e.g., methanol or ethanol) is present in an amount ranging from 5% to 15% per total volume of the mobile phase. In another embodiment, the modifier described herein (e.g., methanol or ethanol) is present in an amount ranging from 5% to 10% per total volume of the mobile phase.

Mobile phases described herein can be passed through the column via isocratic or gradient-based methods. Isocratic, or isocratic flow, means that the composition of the mobile phase (e.g., a mixture of $CO_2$ and ethanol) is kept constant and uniform throughout the separation. Gradient, or gradient flow, means the composition of the mobile phase (e.g., a mixture of $CO_2$ and ethanol) varies. For example, when a mobile phase is defined as having specific volume percentages of modifier, such as in the case of an amount ranging from 1% to 30% per total volume of the mobile phase, it is to be understood that both isocratic flow (e.g., a defined amount ranging from 1% to 30% per total volume of the mobile phase held constant and uniform throughout the separation) and gradient flow (e.g., amounts ranging from 1% to 30% per total volume of the mobile phase that are varied throughout the separation) is included. In one embodiment, however, the methods described herein comprise isocratic flow, i.e., the isomer (or isomers) of THC is eluted isocratically.

Depending upon the nature of the sample, the methods described herein can be used as means to identify the presence or absence of one or more isomers of THC selected from those described. Thus, in one embodiment, at least two isomers of THC are present in the sample and are separated using the $CO_2$-based methods described herein. In another embodiment, at least three isomers of THC are present in the sample and are separated using the $CO_2$-based methods described herein. In a further embodiment, each of the the THC isomers (+)trans-$\Delta^8$-THC, (−)trans-$\Delta^8$-THC, (+)trans-$\Delta^9$-THC, and (−) trans-$\Delta^9$-THC) are present in the sample and are each separated using the $CO_2$-based methods described herein. In another embodiment, the sample may further comprise, in addition to one or more isomers of THC, the cannabinoid cannabidol (CBD). Thus, in one embodiment, CBD may also be identified and/or separated from a sample comprising one or more isomers of THC.

Based upon the mobile phase and column chemistry, retention times of the defined isomers can vary. However, it is advantageous to avoid elution from the solvent void. The present methods accomplish this and, thus, in one embodiment, the retention time of the isomer of THC, or the first isomer of THC when multiple isomers are present, is greater than 1.5 minutes using the $CO_2$-based methods described herein. In another aspect, the retention time of the isomer of THC, or the first isomer of THC when multiple isomers are present, is greater than 1.7 minutes using the $CO_2$-based methods described herein.

As described above, the methods described herein are efficient in separating the predominant isomers of THC and can be used for high-throughput analysis. Thus, in one embodiment, the total elution period of the isomer of THC, or the total elution period for the last eluted isomer of THC when multiple isomers are present, is 6 minutes or less using the $CO_2$-based methods described herein. That is, the total run time to separate the isomer or isomers of THC does not exceed 6 minutes. In another embodiment, the total elution period for the last eluted isomer of THC when multiple isomers are present, is 5.5 minutes or less using the $CO_2$-based methods described herein. In another embodiment, the total elution period of the isomer of THC, or the total elution period for the last eluted isomer of THC when multiple isomers are present, is 5 minutes or less using the $CO_2$-based methods described herein.

The $CO_2$-Based System and Method of Use $CO_2$-based chromatography systems, as well as related components, that can be used in the present methods are described in e.g., U.S. Patent Application Publication Nos. 2015/0331001 and 2014/0157871 and International Application Publication Nos. WO 2013/134468, WO 2013/134473, WO 2013/134471, WO 2013/134476, WO 2013/134475, WO 2013/134485, WO 2013/134483, WO 2013/134478, and WO 2013/134496, each of which are incorporated herein by reference.

Figure 6:
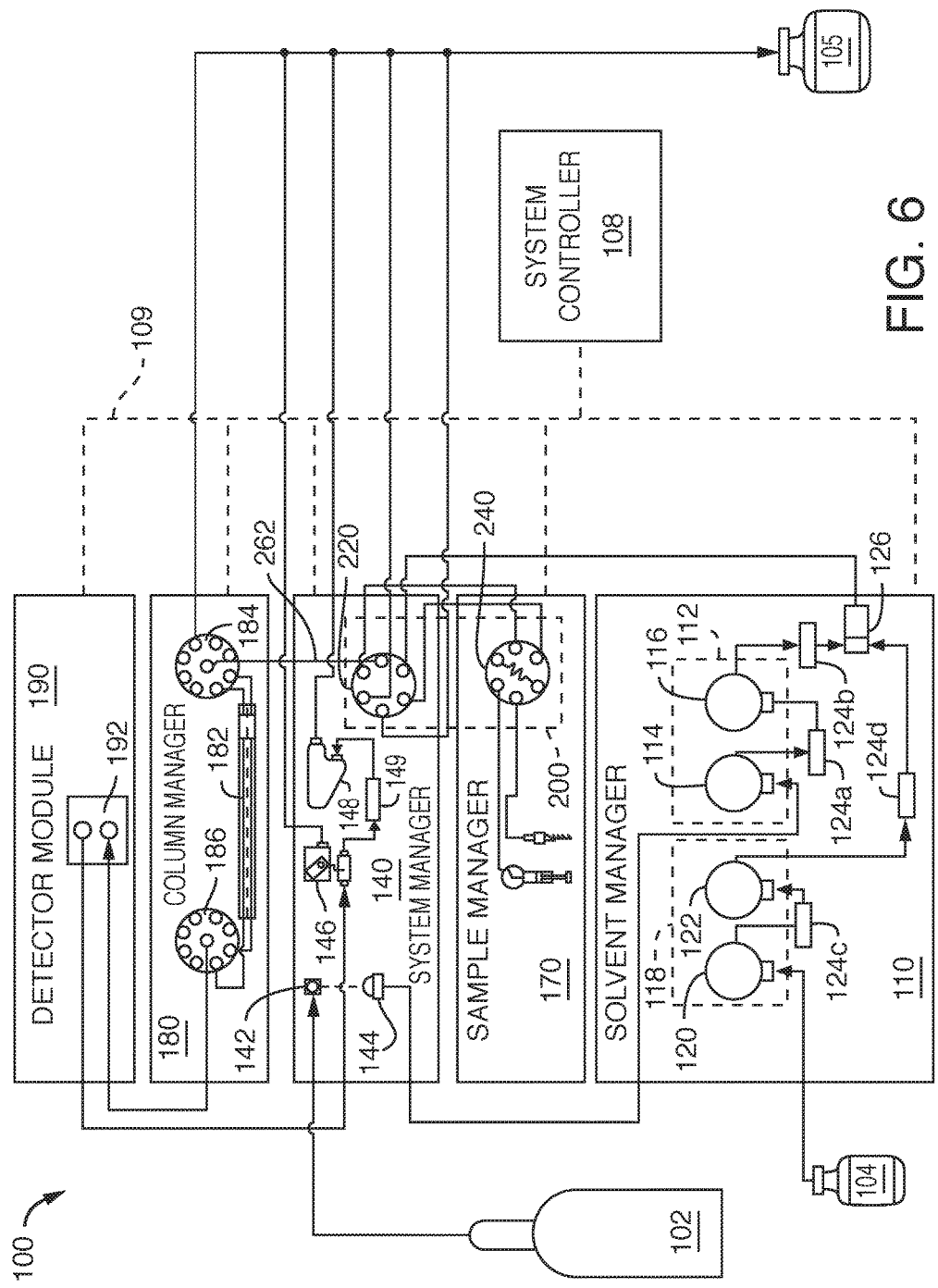
FIG. 6 is a schematic view of an exemplary $CO_2$-based chromatography system for use in the methods described herein.

For example, FIG. 6 illustrates an exemplary and basic diagram of a $CO_2$ based system from the above disclosures, and which can be used to facilitate the methods described herein. As depicted, the $CO_2$ based system 100 comprises a plurality of stackable modules including a solvent manager 110; a system manager 150; a sample manager 170; a column manager 180; and a detector module 190.

By way of illustration, the solvent manager 110 is comprised of a first pump 112 which receives carbon dioxide from $CO_2$ source 102 (e.g., a tank containing compressed $CO_2$). The $CO_2$ passes through an inlet shutoff valve 142 and a filter 144 in the system manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable to e.g., liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

Also by way of illustration, the solvent manager 110 also includes a second pump 118 for receiving an organic co-solvent (e.g., methanol, etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

Also by way of illustration, transducers 124a-d are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows are mixed at a tee 126 forming a mobile phase fluid flow that continues to an injection valve subsystem 200, which injects a sample slug for separation into the mobile phase fluid flow.

Also by way of illustration, the injection valve subsystem 200 is comprised of an auxiliary valve 220 that is disposed in the system manager 140 and an inject valve 240 that is disposed in the sample manager 170. The auxiliary valve 220 and the inject valve 240 are fluidically connected and the operations of these two valves are coordinated in such a manner as to reduce sample carryover and system pressure perturbations occurring during injection. The reduced system pressure perturbations eliminate back flow in the column that may occur during injection and as the result of system pressure drops. The system manager 140 includes a valve actuator for actuating the auxiliary valve 220 and electrical drives for driving the valve actuations. Similarly, the sample manager 170 includes a valve actuator for actuating the inject valve and electrical drives for driving the valve actuations.

Also by way of illustration, from the injection valve subsystem 200, the mobile phase flow containing the injected sample slug continues through a separation column 182 in the column manager 180, where the sample slug is separated into its individual component parts. The column manager 180 comprises a plurality of such separation columns, and inlet and outlet switching valves 184, 186 for switching between the various separation/chromatography columns.

Also by way of illustration, after passing through the separation column 182, the mobile phase fluid flow continues on to a detector 192 (e.g., a flow cell/photodiode array type detector) housed within the detector module 190 then through a vent valve 146 and then on to a back pressure regulator 148 in the system manager 140 before being exhausted to waste 106. A transducer 149 is provided between the vent valve 146 and the back pressure regulator 148.

Also by way of illustration, the back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. The back pressure regulator 148 can be used to maintain the system pressure in the range of 1000 psi to 9000 psi e.g., in the range of 1000 psi to 6000 psi, or e.g., in the range of 1000 psi to 4000 psi, or at any particular pressure within these ranges.

Also by way of illustration, also shown schematically in FIG. 6 is a computerized system controller 108 that can assist in coordinating operation of the $CO_2$ based system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. Some or all of the various features of these control electronics can be integrated in a microcontroller.

Figure 7:
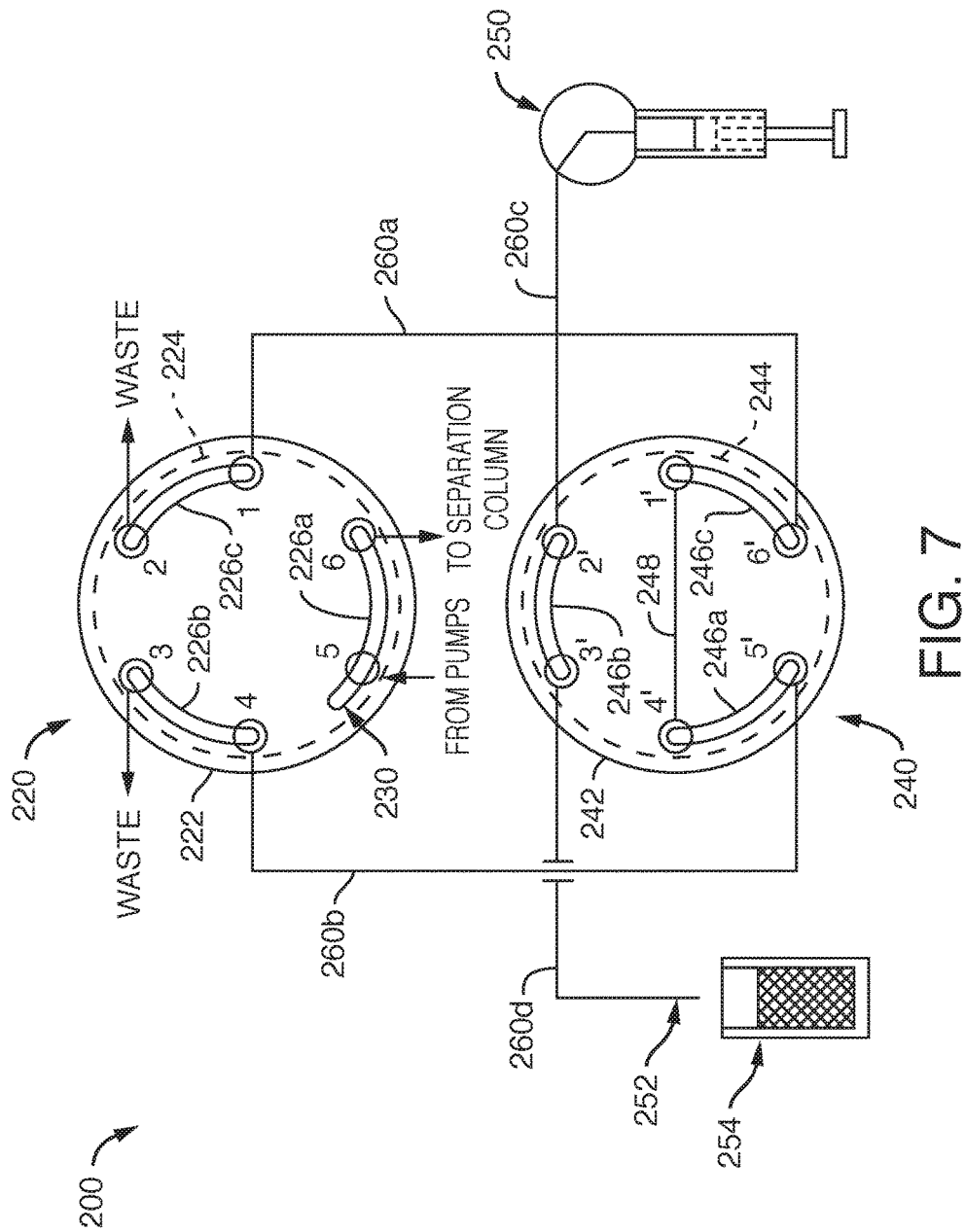
FIG. 7 is a schematic view of an exemplary injection valve for the $CO_2$-based system shown in FIG. 6.

Also by way of illustration, the injection valve subsystem 200 including the auxiliary valve 220 and the inject valve 240 is illustrated in FIG. 7. The auxiliary valve 220 is a rotary shear valve that includes an auxiliary valve stator 222 that has a plurality of ports, numbered 1 through 6 in FIG. 7, and an auxiliary valve rotor 224 that has a rotor interface, which includes three fluid conduits in the form of arcuate grooves 226a-c. When assembled, the rotor interface is urged into contact with the auxiliary valve stator 222, e.g., by pressure exerted on the auxiliary valve rotor 224 by a spring, to help ensure a fluid-tight seal there between. The ports 1-6 are configured to receive fittings (e.g., standard compression screw/ferrule type fittings) for coupling fluidic tubing to the auxiliary valve stator 222. In some aspects, the auxiliary valve rotor 224 can be rotated to three discrete angular positions, relative to the auxiliary valve stator 222, to connect the rotor grooves 226a-c with different ones of the stator ports 1-6 to form different fluidic passageways. One of the grooves, groove 226a, includes an extended portion 230 which allows the auxiliary valve rotor 224 to be rotated to a position in which the groove 226a forms a fluidic pathway between stator ports 4 and 5, while ports 1-3 and 6 are dead ended.

Also by way of illustration, the inject valve 240 is another six-port rotary shear valve that includes an inject valve stator 242 having a plurality of ports, numbered 1' through 6' in FIG. 7, and an inject valve rotor 244. The inject valve rotor 244 has a rotor interface, which includes three fluid conduits in the form of arcuate grooves 246a-c. When assembled, the rotor interface is urged into contact with the inject valve stator 242, e.g., by pressure exerted on the inject valve rotor 244 by a spring, to help ensure a fluid-tight seal there between. The ports 1'-6' are configured to receive fittings (e.g., standard compression screw/ferrule type fittings) for coupling fluidic tubing to the inject valve stator 242. Port 1' is fluidically connected to port 4' via a sample loop 248 (e.g., fluidic tubing external to the inject valve stator 242). Port 2' is fluidically connected to a metering syringe 250 and port 3' is connected to a needle 252. The metering syringe 250 and needle 252 are disposed within the sample manager 170 and are operable to aspirate sample from vials 254 also in the sample manager 170. Port 5' of the inject valve 240 is connected to port 4 of the auxiliary valve 220, and port 6' of the inject valve 240 is connected to port 1 of the auxiliary valve 220. The connections between port 2' and the syringe 250, between port 3' and the needle 252, between port 5' and port 4, and between port 6' and port 1 are made via the fluidic tubing 260a-d.

Also by way of illustration, the inject valve rotor 244 can be rotated to two discrete angular positions, relative to the inject valve stator 242, to connect the rotor grooves 246a-c with different ones of the stator ports 1'-6' to form different fluid passageways.

In some aspects, the pressure at the exit of the system, as controlled by the automated backpressure regulator (ABPR) in the $CO_2$-based system of the subject technology is from about 1000 psi to about 9000 psi, or any pressures there between. In some aspects, the backpressure is any pressure between the range of about 1000 psi to about 6000 psi. In another aspect, the ABPR is set at 1700 psi, 2200 psi, 2500 psi, 2900 psi, 3200 psi, 3500 psi. In one aspect, overall, the ABPR of the $CO_2$-based systems provide steady pressure levels and improved pressure gradients.

In the $CO_2$-based systems, temperature fluctuations in the pumping systems which may result in system pressure fluctuations are also reduced or eliminated. This leads to a reduced baseline noise of chromatograms of the $CO_2$ based system of the subject technology. Alternatively or in addition, the $CO_2$-based systems that can be used in the methods described herein minimize the consumption of mobile phase solvents (e.g. methanol, acetonitrile, etc.) thereby generating less waste for disposal and reducing the cost of analysis (by more than 100 fold, in some cases) per sample.

Exemplary processes for operating the $CO_2$ based systems described herein are described in e.g., U.S. Patent Application Publication Nos. 2015/0331001 and 2014/0157871, each of which are incorporated herein by reference.

Column Chemistries

The solid stationary phase of the chromatography columns of the $CO_2$ based system includes porous inorganic or inorganic/organic hybrid particles with the mechanical stability and structural integrity required to withstand the operating pressures of the system.

Inorganic particles suitable for use in the system and method of the subject technology include e.g., silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In certain aspects, such inorganic particles may have no surface modifications. For example, without surface modifications, silica is characterized by the presence of silanol groups on its surface. In other aspects, the inorganic particles, e.g., silica, may have been surface modified. For example, silica can be surface modified or derivatized with an organic polar or nonpolar functional group such as butyl (C4), octyl (C8), octadecyl (C18), triacontyl (C30), phenyl, amino, cyano, etc. In one embodiment, the particles in the chromatography columns used herein comprise modified polysaccharide-coated silica-based particles. Exemplary commercially available columns that include such particles and which are suitable for the methods described herein include, for example, the ACQUITY UPC2 Trefoil AMY1 Column, ACQUITY UPC2

Trefoil CEL1 Column, and ACQUITY UPC2 Trefoil CEL2 Column from Waters Technologies Corporation, Milford, Mass.

Hybrid particles suitable for use in the system and method of the subject technology include an inorganic portion such as, e.g., alumina, silica, titanium or zirconium oxides, or ceramic material; and an organic portion bonded to one or more atoms of the inorganic portion. Exemplary hybrid materials are disclosed in e.g., U.S. Pat. No. 4,017,528, the contents of which is incorporated herein by reference.

In some aspects, the organic portion of the hybrid particles is a C1-C18 aliphatic or aromatic moieties (which may additionally be substituted with alkyl, aryl, cyano, amino, hydroxyl, diol, nitro, ester, ion exchange or embedded polar functionalities) or a substituted or unsubstituted C1-C18 alkylene, alkenylene, alkynylene or arylene moiety. In one aspect, where the inorganic portion is silica, "hybrid silica" refers to a material having the formula $SiO_2/(R^2_pR^4_qSiO_t)_n$ or $SiO_2/[R^6(R^2_rSiO_t)_m]_n$ (disclosed in U.S. Pat. Nos. 7,919, 177; 7,223,473, and 6,686,035, each of which is hereby incorporated herein by reference) wherein $R^2$ and $R^4$ are independently C1-C18 aliphatic or aromatic moieties (which may additionally be substituted with alkyl, aryl, cyano, amino, hydroxyl, diol, nitro, ester, ion exchange or embedded polar functionalities), $R^6$ is a substituted or unsubstituted C1-C18 alkylene, alkenylene, alkynylene or arylene moiety bonded to one or more silicon atoms or bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, or alternatively, 0.1 to 1, or alternatively 0.2 to 0.5. $R^2$ may be additionally substituted with a functionalizing group R.

The functionalizing group R includes organic functional groups which impart a certain chromatographic functionality to a chromatographic stationary phase, including, e.g., octadecyl (C18) or phenyl. Such functionalizing groups are present in, e.g., surface modifiers such as disclosed herein which are attached to the base material, e.g., via derivatization or coating and later cross slinking, imparting the chemical character of the surface modifier to the base material. In one aspect, such surface modifiers have the formula $Z_a(R')_bSi$—R, where Z=Cl, Br, I, C1-C5 alkoxy, dialkylamino, e.g., dimethylamino, or trifluoromethanesulfonate; a and b are each an integer from 0 to 3 provided that a+b=3; R' is a C1-C6 straight, cyclic or branched alkyl group, and R is a functionalizing group. R' may be, e.g., methyl, ethyl, propyl, isopropyl, butyl, t-butyl, secbutyl, pentyl, isopentyl, hexyl or cyclohexyl. In one aspect, R' is methyl.

The porous inorganic/organic hybrid particles possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later crosslinking, imparting the chemical character of the surface modifier to the base material. In one aspect, the organic groups of the hybrid particle react to form an organic covalent bond with a surface modifier. The surface modifiers can form an organic covalent bond to the particle's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds.

In one embodiment, the solid stationary phase of the chromatography columns herein include a monolith, particles, porous particles, and/or superficially porous particles. Particles can be spherical or non-spherical. The solid stationary phase can include silica, inorganic silica, and/or metal oxide. In one embodiment, the column is equipped with one or more frits to contain the stationary phase material. In aspects in which the stationary phase material is monolithic, the housing may be used without the inclusion of one or more frits.

The solid stationary phase includes, for example, particles having a mean size within the range of about 0.5-3.5 microns, though a smaller or larger size could be selected if appropriate for a desired application. In one embodiment, the mean particle size is 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5 microns. In general, particle size can be selected in view of the desired pressure and/or flow rate. For example, larger particle size can be used to achieve consistent pressure from a column head to an end during high pressurized digestion. Alternatively, smaller particle sizes result in higher flow rates and higher efficiency, which yield faster and more sensitive separations. In one embodiment, particles defined herein have an average particle size of 2.5 μm. The solid stationary phase can include pores having a mean pore volume within the range of 0.1-2.5 cm/g. In one embodiment, the mean pore volume is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm/g. In some aspects, porous particles may be advantageous because they provide a relatively large surface area (per unit mass or column volume) for protein coverage at the same time as the ability to withstand high pressure.

The solid stationary phase can include pores having a mean pore diameter within the range of 100-1000 Angstroms. For example, in some aspects, the mean pore diameter of the solid stationary phase particles is about 100, 200, 300, 400, 500, 600, 700, 800, 900, 1000 Angstroms, or any value or range there between.

In one aspect, the chromatography or separation column herein includes (a) a column having a cylindrical interior for accepting a packing material, and (b) a packed chromatographic bed comprising a porous material comprising an organosiloxane/$SiO_2$ material having the formula $SiO_2/(R^2_pR^4_qSiO_t)n$ or $SiO_2/[R^6(R^2_rSiO_t)_m]_n$, as described above, wherein $R^2$ and $R^4$ are independently C1-C18 aliphatic, styryl, vinyl, propanol, or aromatic moieties, $R^6$ is a substituted or unsubstituted C1-C18 alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, said porous hybrid silica chromatographic matrix having a chromatographically-enhancing pore geometry and average pore diameters of about 100 to 300 A. In one aspect, the porous particles of hybrid silica have been surface modified. In another aspect, the particles have been surface modified by a surface modifier selected from the group consisting of an organic group surface modifier, a silanol group surface modifier, a polymeric coating surface modifier, and combinations thereof. In another aspect, the surface modifier has the formula $Z_a(CR')_b Si$—R, where Z=Cl, Br, I, C1-C5 alkoxy, dialkylamino or trifluoromethanesulfonate; a and b are each an integer from 0 to 3 provided that a+b=3; R' is a C1-C6 straight, cyclic or branched alkyl group, and R is a functionalizing group.

The functionalizing group R may include alkyl, alkenyl, alkynyl, aryl, cyano, amino, diol, nitro, cation or anion exchange groups, or alkyl or aryl groups with embedded polar functionalities. Examples of suitable R functionalizing groups include C1-C30 alkyl, including C1-C20, such as octyl (C8), octadecyl (C18), and triacontyl (C30); alkaryl, e.g., C1-C4-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the contents of which is incorporated herein by reference. In one aspect, the surface modifier is an organotrihalosilane, such as octyltrichlorosilane or octadecyltrichlorosilane. In another aspect, the surface modifier may be a halopolyorganosilane, such as octyldimethylchlorosilane or octadecyldimethylchloro silane.

In one aspect, the hybrid particle's organic groups and silanol groups are both surface modified or derivatized. In another aspect, the particles are surface modified by coating with a polymer. In certain aspects, surface modification by coating with a polymer is used in conjunction with silanol group modification, organic group modification, or both silanol and organic group modification.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III), and chemisorption of pre synthesized polymers onto the surface of the support (type IV). See, e.g., Hanson et al., J. Chromat. A656 (1993) 369-380, the contents of which is incorporated herein by reference. As noted above, coating the hybrid material with a polymer may be used in conjunction with various surface modifications described in U.S. Pat. Nos. 7,919,177; 7,223, 473, and 6,686,035, each of which are incorporated herein by reference. Additional inorganic/organic hybrid particles are disclosed in e.g., WO 2010/141426, which is hereby incorporated herein by reference.

In one embodiment, the internal diameter (ID) of the chromatography column in the methods described herein is about 1 mm to 5 mm, or 2 mm to 4 mm, or 2.0 mm to 3.0 mm. In one embodiment, the ID of the column is 3 mm. In some embodiments, the length of the chromatography column is 30 mm to 200 mm or 50 mm to 150 mm. In one embodiment, the length of the chromatography column is about 50 mm. In one embodiment, the length of the chromatography column is about 100 mm. In another embodiment, the length of the chromatography column is about 150 mm.

In one embodiment, the particles and columns used in the methods described herein have the following specifications:

| Chemistry | Particle Shape | Particle Size (μm) | Internal Diameter (mm) | Length (mm) |
|---|---|---|---|---|
| Exemplified Column 1: Silica-based particles with modified polysaccharide-based surface (e.g., Trefoil AMY1, Waters Technologies Corporation, Milford, MA) | Spherical | 2.5 | 3 | 150 |
| Exemplified Column 2: Silica-based particles with modified polysaccharide-based surface (e.g., Trefoil CEL1, Waters Technologies Corporation, Milford, MA) | Spherical | 2.5 | 3 | 150 |
| Exemplified Column 3 Silica-based particles with modified polysaccharide-based surface modification/polymer coating (e.g., Trefoil CEL2, Waters Technologies Corporation, Milford, MA) | Spherical | 2.5 | 3 | 150 |

In one embodiment, depending on the column dimension chosen and optimization necessary, the flow rate of the mobile phase is set between about 0.1 mL/min to 4 mL/min, or any intervals there between, e.g., 0.5 mL/min to 3.5 mL/min, or at 1.0 mL/min, with a backpres sure regulator setting of about 1000-9000 psi or about 2000-8000 psi, or about 3000-6000 psi, or about 4000-5000 psi. In other embodiments, the temperature at which the chromatography column operates is adjusted to a practical working range of about 5° C. to 85° C., or any specific temperature within this range. In some embodiments, the column compartment temperature ranges from about 20° C. to 70° C.

Kits and Computer Mediums

Kits for quantifying the predominant isomers of THC using the $CO_2$-based chromatography methods and apparatus described herein are also provided. In one embodiment, a kit may comprise a first known quantity of a first calibrator, a second known quantity of a second calibrator, and optionally comprising one or more predominant isomers of THC, wherein the first known quantity and the second known quantity are different, and wherein the first calibrator, the second calibrator, and the one or more predominant isomers of THC are each distinguishable in a single sample by chromatography.

The kits described herein may also comprise instructions for: (i) obtaining a mass spectrometer signal comprising a first calibrator signal, a second calibrator signal, and one or more predominant isomers of THC from a single sample comprising the first known quantity of the first calibrator, the second known quantity of the second calibrator, and optionally comprising one or more predominant isomers of THC; and (ii) quantifying one or more predominant isomers of THC in the single sample using the first calibrator signal, the second calibrator signal, and the signal of the one or more predominant isomers of THC.

Computer readable mediums for use with the $CO_2$-based chromatography methods and apparatus are also provided. In an exemplary embodiment, a computer readable medium may comprise computer executable instructions adapted to: separating one or more predominant isomers of THC as described herein and obtaining a mass spectrometer signal comprising a first known quantity of a first calibrator, a second known quantity of a second calibrator, and optionally comprising one or more predominant isomers of THC, wherein the first known quantity and the second known quantity are different, and wherein the first calibrator, the second calibrator, and the one or more predominant isomers of THC are each distinguishable in a single sample by mass spectrometry.

The computer readable medium may further comprise executable instructions adapted to quantify one or more predominant isomers of THC in a single sample using the first calibrator signal, the second calibrator signal, and the signal of the one or more predominant isomers of THC.

The subject technology is further illustrated by the following examples which should not be construed as limiting. The contents of all references, patents and published patent applications cited throughout this application, are incorporated herein by reference.

Exemplification

Separation of (+)trans-$\Delta^8$-THC, (−)trans-$\Delta^8$-THC, (+)trans-$\Delta^9$-THC, and (−)trans-$\Delta^9$-THC (+)trans-$\Delta^8$-THC, (−)trans-$\Delta^8$-THC, (+)trans-$\Delta^9$-THC, and (−)trans-$\Delta^9$-THC were purchased from Cerilliant® Corporation, Round Rock, Tex. The four isomers were diluted and mixed to afford a sample containing 0.0125 mg/mL of each isomer.

The sample was injected into the $CO_2$-based chromatography system for analysis with the following conditions.

Method 1
Mobile Phase A: $CO_2$
Mobile Phase B/Co-Solvent (modifier): Ethanol
Chromatographic Column: Exemplified Column 1, 2.5 μm, 3×150 mm (Trefoil AMY1, Waters Technologies, Milford, Mass.)
LC Flow Rate: 2 mL/min
LC Isocratic: 15% EtOH
Column Temperature: 50° C.
APBR: 2000 psi
Detection: 228 nm The results from Method 1 are shown in FIG. 1. As shown, separation was achieved for (+)trans-$\Delta^8$-THC, (−)trans-$\Delta^8$-THC, (+)trans-$\Delta^9$-THC, and (−)trans-$\Delta^9$-THC with retention times at 1.71, 1.54, 1.94, and 2.46 minutes respectively. While the total run time was about 6 minutes, the last predominate isomer was eluted by about 2.7 minutes. This data not only shows that the present methods are highly effective in separating (+)trans-$\Delta^8$-THC, (−)trans-$\Delta^8$-THC, (+)trans-$\Delta^9$-THC, or (−)trans-$\Delta^9$-THC, but it also supports the high throughput and efficient nature to which the present methods comply, i.e., (+)trans-$\Delta^8$-THC, (−)trans-$\Delta^8$-THC, (+)trans-$\Delta^9$-THC, and (−)trans-$\Delta^9$-THC were separated from a single sample under about 2.7 minutes.

Figure 2:
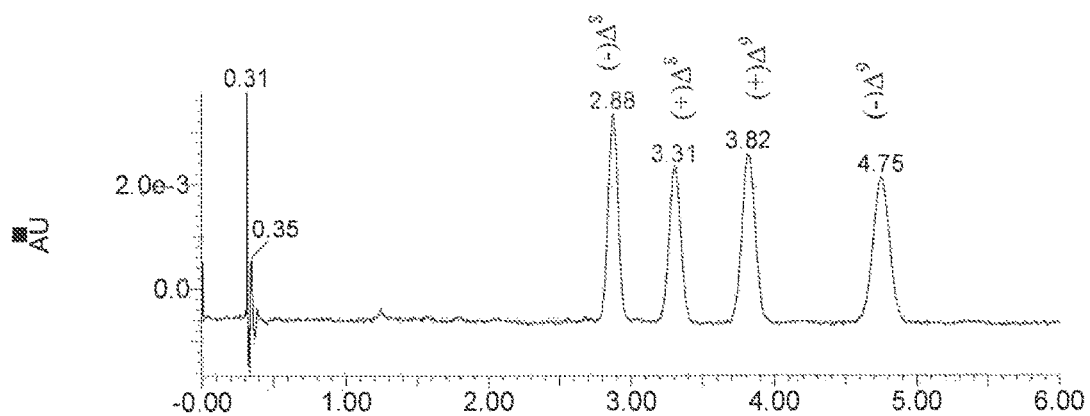
FIG. 2 depicts a chromatogram of the separation of (+)trans-$\Delta^8$-THC, (−)trans-$\Delta^8$-THC, (+)trans-$\Delta^9$-THC, and (−)trans-$\Delta^9$-THC using a Trefoil AMY1 column and 10% ethanol following the $CO_2$-based chromatography methods described herein.

Method 2
Mobile Phase A: $CO_2$
Mobile Phase B/Co-Solvent (modifier): Ethanol
Chromatographic Column: Exemplified Column 1, 2.5 μm, 3×150 mm (Trefoil AMY1, Waters Technologies, Milford, Mass.)
Flow Rate: 2 mL/min
Isocratic: 10% EtOH
Column Temperature: 50° C.
APBR: 2000 psi
Detection: 228 nm The results from Method 2 are shown in FIG. 2. Effective separation was achieved for (+)trans-$\Delta^8$-THC, (−)trans-$\Delta^8$-THC, (+)trans-$\Delta^9$-THC, and (−)trans-$\Delta^9$-THC with retention times of 3.31, 2.88, 3.82, and 4.75 minutes respectively, and the last isomer eluted in less than 5 minutes. This method shows that separation using the disclosed methods is also achievable under alternative conditions such as lower co-solvent percentages. This allows for greater flexibility e.g., in instances of matrix interferences.

Figure 3:
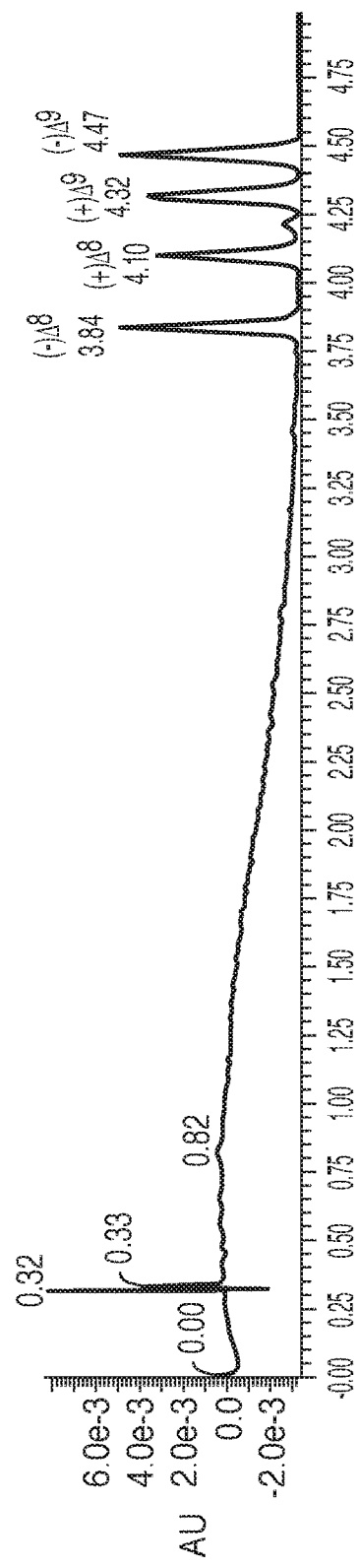
FIG. 3 depicts a chromatogram of the separation of (+)trans-$\Delta^8$-THC, (−)trans-$\Delta^8$-THC, (+)trans-$\Delta^9$-THC, and (−)trans-$\Delta^9$-THC using a Trefoil AMY1 column and 2-20% ethanol gradient following the $CO_2$-based chromatography methods described herein.

Method 3
Mobile Phase A: $CO_2$
Mobile Phase B/Co-Solvent (modifier): Ethanol
Chromatographic Column: Exemplified Column 1, 2.5 μm, 3×150 mm (Trefoil AMY1, Waters Technologies, Milford, Mass.)
Flow Rate: 2 mL/min
Gradient: 2-20% EtOH over 5 min.
Column Temperature: 50° C.
APBR: 2000 psi
Detection: 228 nm The results from Method 3 are shown in FIG. 3. (+)trans-$\Delta^8$-THC, (−)trans-$\Delta^8$-THC, (+)trans-$\Delta^9$-THC, and (−)trans-$\Delta^9$-THC were again effectively separated and had retention times of 4.10, 3.84, 4.32, and 4.47 minutes respectively. The last isomer eluted in less than 4.6 minutes and this method provides another example where separation using the present methods is achievable under alternative conditions (gradient method vs. isocratic method), thereby allowing for greater flexibility.

Figure 4:
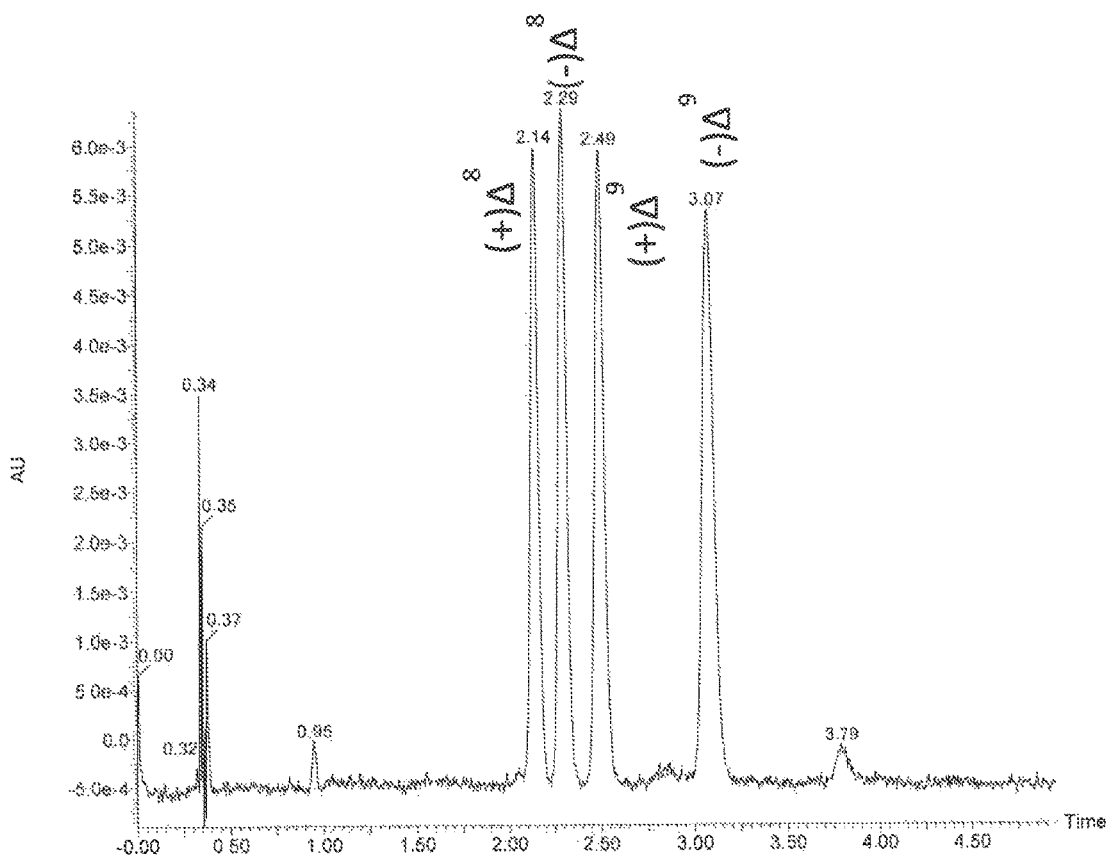
FIG. 4 depicts a chromatogram of the separation of (+)trans-$\Delta^8$-THC, (−)trans-$\Delta^8$-THC, (+)trans-$\Delta^9$-THC, and (−)trans-$\Delta^9$-THC using a Trefoil CEL1 column and 7% ethanol following the $CO_2$-based chromatography methods described herein.

Method 4
Mobile Phase A: $CO_2$
Mobile Phase B/Co-Solvent (modifier): Ethanol Chromatographic Column: Exemplified Column 2, 2.5 μm, 3×150 mm (Trefoil CEL1, Waters Technologies, Milford, Mass.)
Flow Rate: 2 mL/min
Isocratic: 7% EtOH
Column Temperature: 50° C.
APBR: 2000 psi
Detection: 228 nm The results from Method 4 are shown in FIG. 4. Effective separation was achieved for (+)trans-$\Delta^8$-THC, (−)trans-$\Delta^8$-THC, (+)trans-$\Delta^9$-THC, and (−)trans-$\Delta^9$-THC, with retention times of 2.14, 2.29, 2.49, and 3.07 minutes respectively. The last isomer eluted in less than 3.2 minutes and the total run time did not exceed 5 minutes. This data shows that the present methods are amendable for use with various column chemistries, and e.g., with those which are commercially available.

Figure 5:
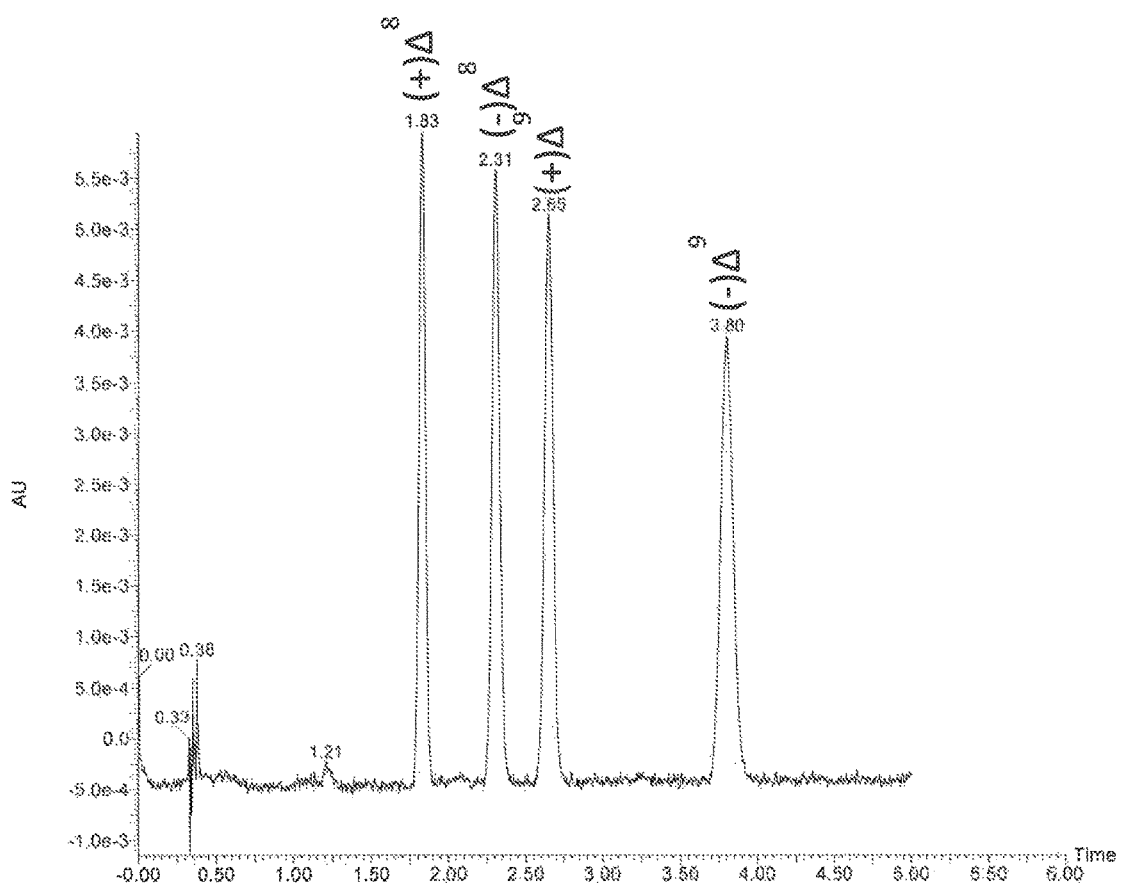
FIG. 5 depicts a chromatogram of the separation of (+)trans-$\Delta^8$-THC, (−)trans-$\Delta^8$-THC, (+)trans-$\Delta^9$-THC, and (−)trans-$\Delta^9$-THC using a Trefoil CEL2 column and 5% ethanol following the $CO_2$-based chromatography methods described herein.

Method 5
Mobile Phase A: $CO_2$
Mobile Phase B/Co-Solvent (modifier): Ethanol
Chromatographic Column: Exemplified Column 3, 2.5 μm, 3×150 mm (Trefoil CEL2, Waters Technologies, Milford, Mass.)
Flow Rate: 2 mL/min
Isocratic: 5% EtOH
Column Temperature: 50° C.
APBR: 2000 psi
Detection: 228 nm The results from Method 5 are shown in FIG. 5. Effective separation was achieved for (+)trans-$\Delta^8$-THC, (−)trans-$\Delta^8$-THC, (+)trans-$\Delta^9$-THC, and (−)trans-$\Delta^9$-THC having retention times of 1.83, 2.31, 2.65, and 3.08 minutes respectively. The last isomer eluted in less than 4.0 minutes and the total run time did not exceed 6 minutes. This data is yet another example to which the present methods are shown to be amendable for use with various column chemistries, and e.g., with those which are commercially available.

As seen from Methods 1 to 5, optimal, efficient, and versatile separation is achieved between (+)trans-$\Delta^8$-THC, (−)trans-$\Delta^8$-THC, (+)trans-$\Delta^9$-THC, and (−)trans-$\Delta^9$-THC using the methods described herein.

The invention claimed is:

1. A method of separating an isomer of THC selected from (+)trans-$\Delta^8$-THC, (−)trans-$\Delta^8$-THC, (+)trans-$\Delta^9$-THC, and (−)trans-$\Delta^9$-THC using $CO_2$-based chromatography, comprising
injecting a sample comprising the isomer of THC into a $CO_2$-based mobile phase;
flowing the $CO_2$-based mobile phase and sample into a CO2-based chromatography system having a 150 mm length and 3 mm internal diameter column including a stationary phase disposed within the column, the stationary phase comprising modified polysaccharide-coated silica-based particles with a particle size of 2.5 µm at a rate of 2 mL/min; and
eluting the isomer of THC from the chromatography column using a mobile phase comprising $CO_2$ and ethanol, wherein the retention time of the isomer of THC, or the first isomer of THC when multiple isomers are present, is greater than 1.5 minutes, and the total elution period of the isomer of THC, or the total elution period for the last eluted isomer of THC when multiple isomers are present, is 6 minutes or less, wherein a resolution of each pair of isomers is greater than about 2.

2. The method of claim 1, wherein the ethanol is present in an amount ranging from 1% to 30% per total volume of the mobile phase.

3. The method of claim 1, wherein the ethanol is present in an amount ranging from 3% to 25% per total volume of the mobile phase.

4. The method of claim 1, wherein the ethanol is present in an amount ranging from 5% to 20% per total volume of the mobile phase.

5. The method of claim 1, wherein the ethanol is present in an amount ranging from 5% to 15% per total volume of the mobile phase.

6. The method of claim 1, wherein the ethanol is present in an amount ranging from 5% to 10% per total volume of the mobile phase.

7. The method of claim 1, wherein the isomer of THC is eluted isocratically.

8. The method of claim 1, wherein at least two isomers of THC are present in the sample and separated.

9. The method of claim 1, wherein at least three isomers of THC are present in the sample and separated.

10. The method of claim 1, wherein each of (+)trans-$\Delta^8$-THC, (−)trans-$\Delta^8$-THC, (+)trans-$\Delta^9$-THC, and (−)trans-$\Delta^9$-THC are present in the sample and separated.

11. The method of claim 1, wherein the retention time of the isomer of THC, or the first isomer of THC when multiple isomers are present, is greater than 1.7 minutes.

12. The method of claim 1, wherein the total elution period of the isomer of THC, or the total elution period for the last eluted isomer of THC when multiple isomers are present, is 5.5 minutes or less.

13. The method of claim 1, wherein the total elution period of the isomer of THC, or the total elution period for the last eluted isomer of THC when multiple isomers are present, is 5 minutes or less.

* * * * *